United States Patent [19]

Koda et al.

[11] Patent Number: 5,049,551
[45] Date of Patent: Sep. 17, 1991

[54] 5-FLUOROURACIL, 2'-DEOXY-5-FLUOROURIDINE AND 1-CARBOMOYL-5-FLUOROURACIL COMPOUNDS

[75] Inventors: Akihide Koda, Gifu; Jun'ichiro Kita, Ube; Yoshio Kaku, Ube; Iichiro Horimi, Ube; Osami Sakamoto, Ube, all of Japan

[73] Assignee: UBE Industries, Ltd., Ube, Japan

[21] Appl. No.: 528,710

[22] Filed: May 24, 1990

[30] Foreign Application Priority Data

May 30, 1989 [JP] Japan .................................. 1-134806
Jul. 6, 1989 [JP] Japan .................................. 1-173122

[51] Int. Cl.$^5$ .................. A61K 31/505; A61K 31/70; C07H 19/06; C07D 239/02
[52] U.S. Cl. ...................................... 514/50; 514/269; 536/23; 544/309; 544/310; 544/311
[58] Field of Search .................. 536/23; 544/309, 310, 544/311; 514/50, 269

[56] References Cited

PUBLICATIONS

Fuji Kagaku Kogyo Co. Ltd., Chem. Abst. 95-187673y (1981).
Tokyo Kinzoku Kogyo Co. Ltd., Chem. Abstract; 95-150701e (1981).
Takaya et al., Chem. Abst. 98-34595m (1983).
Mitsui Pharmaceuticals, Inc., Chem. Abst. 99-10862r (1983).
Yoshizawa et al., Chem. Abst. 108-112481n (1988).
DiGabriele et al., Chem. Abst. 111-2813b (1989).

*Primary Examiner*—Cecilia Shen
*Attorney, Agent, or Firm*—Frishauf, Holtz, Goodman & Woodward

[57] ABSTRACT

A 5-fluorouracil derivative represented by the formula (1):

wherein A represents a group represented by or $-C(=O)-NH-X-NHR^4$ wherein $R^1$ represents a hydrogen atom or $OR^5$ group, $R^2$, $R^3$ and $R^5$ may be the same or different and each represents a hydrogen atom or a group represented by the following formula (2):

$$R^6-NH-CH(R^7)-(CH_2)_n-CO- \quad (2)$$

wherein $R^6$ represents an acyl group, $R^7$ represents a hydrogen atom, a straight or branched alkyl group, a cycloalkyl group, an aralkyl group, a lower alkenyl group or a phenyl group, and n is an integer of 0 to 6,
provided that at least one of $R^2$, $R^3$ and $R^5$ is a group represented by the formula (2), and the case wherein
$R^2$ and $R^5$ are both hydrogen atoms is excluded,
$R^4$ represents a group represented by the formula (2), and X represents an alkylene group or a cycloalkylene group,
and an antitumor agent containing the same as an active ingredient.

15 Claims, No Drawings

5-FLUOROURACIL, 2'-DEOXY-5-FLUOROURIDINE AND 1-CARBOMOYL-5-FLUOROURACIL COMPOUNDS

BACKGROUND OF THE INVENTION

This invention relates to novel 5-fluorouridine, 2'-deoxy-5--fluorouridine and 1-carbamoyl-5-fluorouracil derivatives which have an antitumor effect and are available as a medicine.

A 5-fluorouracil, an antitumor agent synthesized by Duschinsky in 1957, has a wide antitumor spectrum so that it has been used clinically. However, its antitumor activity is insufficient and it has potent toxicity, thus it cannot be necessarily said to be a satisfactory pharmaceutical.

Thus, in order to decrease toxicity possessed by the 5-fluorouracil, 1-(2-tetrahydrofulyl)-5-fluorouracil (general name: Tegafur), 1-n-hexylcarbamoyl-5-fluorouracil (general name: Carmofur), 5'-deoxy-5-fluorouridine (general name Doxifluridine), etc. have been found, but it has been said that their antitumor effects are inferior to that of 5-fluorouracil.

Also, in order to improve the antitumor effect, many attempts to make various derivatives of 5-fluorouridine and 2'-deoxy-5-fluorouridine (e.g. Japanese Provisional Patent Publications No. 77298/1981, No. 92299/1981, No. 91997/ 1982, No. 91998/1982, No. 49315/1983 and No. 134397/1986) have been made, but an available one has not yet been obtained.

Further, regarding providing 1-carbamoyl-5-fluorouracil derivatives which have similar a chemical structure in a part thereof of the compounds of present invention, many attempts have been made as in Japanese Provisional Patent Publications No. 81865/1980, No. 258367/1987 and No. 204171/1986, but a effective one has not yet been obtained.

SUMMARY OF THE INVENTION

An object of the present invention is to provide novel 5-fluorouridine and 2'-deoxy-5-fluorouridine derivatives as well as 1-carbamoyl-5-fluorouracil derivatives which have a more potent antitumor activity and lower toxicity than those of 5-fluorouracil.

The present inventors have conducted intensive studies to develop compounds having a higher antitumor activity and lower toxicity than 5-fluorouracil, and as the result, found that N-acyl-aminocarboxylic acid esters of 5-fluorouridine and 2'-deoxy-5-fluorouridine, and 1-carbamoyl-5-fluorouracil derivatives having a novel structure satisfy the above objects and accomplished the present invention.

That is, the present invention relates to compounds represented by the formula (1):

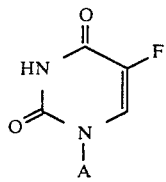 (1)

wherein A represents a group represented by

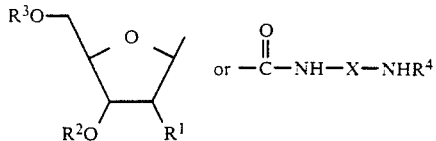 or 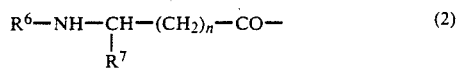

wherein $R^1$ represents a hydrogen atom or $OR^5$ group, $R^2$, $R^3$ and $R^5$ may be the same or different and each represents a hydrogen atom or a group represented by the following formula (2):

$$R^6-NH-CH(R^7)-(CH_2)_n-CO- \quad (2)$$

wherein $R^6$ represents an acyl group, $R^7$ represents a hydrogen atom, a straight or branched alkyl group having 1 to 13 carbon atoms, a cycloalkyl group, an aralkyl group, a lower alkenyl group to which a halogen may be substituted, or a phenyl group to which a lower alkyl, a lower alkenyl or a halogen may be substituted, and n is an integer of 0 to 6, provided that at least one of $R^2$, $R^3$ and $R^5$ is a group represented by the formula (2), and the case wherein $R^2$ and $R^5$ are both hydrogen atoms is excluded, $R^4$ represents a group represented by the formula (2), and X represents an alkylene group having 4 to 12 carbon atoms or a cycloalkylene group, and an antitumor agent containing the same as an active ingredient.

DESCRIPTION OF THE PREFERRED EMBODIMENTS

The compounds of the present invention may be present as a hydrate (monohydrate, ½ hydrate, ¼ hydrate, etc.) and such compounds are also included in the present invention.

As an acyl group represented by $R^6$ in the formula (2), there may be exemplified an alkanoyl group having 1 to 13 carbon atoms such as formyl, acetyl, propionyl, butyryl, isobutyryl, pentanoyl, hexanoyl, octanoyl, 2-propylpentanoyl, decanoyl, undecanoyl, dodecanoyl, tridecanoyl, etc.; an aralkylcarbonyl group such as phenylacetyl, 2-chlorophenylacetyl, 3-chlorophenylacetyl, 4-chlorophenylacetyl, 2-bromophenylacetyl, 3-bromophenylacetyl, 4-bromophenylacetyl, 2-fluorophenylacetyl, 3-fluorophenylacetyl, 4-fluorophenylacetyl, 2-methylphenylacetyl, 3-methylphenylacetyl, 4-methylphenylacetyl, 2-methoxyphenylacetyl, 3-methoxyphenylacetyl, 4-methoxyphenylacetyl, 2-nitrophenylacetyl, 3-nitrophenylacetyl, 4-nitrophenylacetyl, 1-naphthylacetyl, 2-naphthylacetyl, 2-phenylpropionyl, 3-phenylpropionyl, 2-phenylbutyryl, 3-phenylbutyryl, 4-phenylbutyryl, etc.; an aroyl group such as benzoyl, 2-chlorobenzoyl, 3-chlorobenzoyl, 4-chlorobenzoyl, 2,4-dichlorobenzoyl, 2,5-dichlorobenzoyl, 2,6-dichlorobenzoyl, 3,4,5-trichlorobenzoyl, 2-bromobenzoyl, 3-bromobenzoyl, 4-bromobenzoyl, 2-fluorobenzoyl, 3-fluorobenzoyl, 4-fluorobenzoyl, 2-methylbenzoyl, 3-methylbenzoyl, 4-methylbenzoyl, 2,4-dimethylbenzoyl, 2,5-dimethylbenzoyl, 3,4-dimethylbenzoyl, 3,5-dimethylbenzoyl, 2,6-dimethylbenzoyl, 2-methoxybenzoyl, 4-methoxybenzoyl, 2,4-dimethoxybenzoyl, 2,5-dimethoxybenzoyl, 2,6-dimethoxybenzoyl, 3,4-dimethoxybenzoyl, 3,5-dimethoxybenzoyl, 3-cyanobenzoyl, 4- cyanobenzoyl, 2-acetylbenzoyl, 4-acetylbenzoyl, 2-nitrobenzoyl, 3-nitrobenzoyl, 4-nitrobenzoyl, 1-naphthoyl, 2-naphthoyl, etc. Preferably $R^6$ represents an alkanoyl group having 6 to 13 carbon atoms, particularly 2-propylpentanoyl group.

In the formula (2), as the straight or branched alkyl group having 1 to 13 carbon atoms represented by $R^7$ may be exemplified methyl, ethyl, propyl, isopropyl, butyl, isobutyl, pentyl, hexyl, octyl, tridecyl, 11-methyldodecyl, etc. Preferably $R^7$ is a hydrogen atom.

As the cycloalkyl group, cyclohexyl and cyclopentyl can be exemplified.

As the lower alkenyl group to which a halogen may be substituted, there may be exemplified vinyl, 1-fluorovinyl, 2-fluorovinyl, 2,2-difluorovinyl, 2-bromovinyl, 2-iodovinyl, allyl, etc.

As the aralkyl group, benzyl and 2-phenethyl can be exemplified.

As the phenyl group to which a lower alkyl, a lower alkenyl or a halogen may be substituted, there may be exemplified phenyl, 2-bromophenyl, 3-bromophenyl, 4-bromophenyl, 2-chlorophenyl, 3-chlorophenyl, 4-chlorophenyl, 2-fluorophenyl, 3-fluorophenyl, 4-fluorophenyl, 2-tolyl, 3-tolyl, 4-tolyl, 2,5-dimethylphenyl, 3,5-dimethylphenyl, 4-ethylphenyl, 4-vinylphenyl, etc.

n is 0 to 6, and preferably 0.

As the alkylene group and cycloalkylene group represented by X, there may be mentioned tetramethylene, pentamethylene, hexamethylene, heptamethylene, octamethylene, nonamethylene, decamethylene, undecamethylene, 1,2-cyclohexylene, 1,3-cyclohexylene, 1,4-cyclohexylene, etc.

In the following, preparation examples of the compounds represented by the formula (1) are shown.

A compound (1a) of the present invention wherein, in the above formula (1), $R^1$ is a hydrogen atom or $OR^5$ group, and $R^2$, $R^3$ and $R^5$ are groups represented by the formula (2), can be prepared according to the following reaction scheme A by using a compound (3) as a starting material.

<Reaction scheme A>

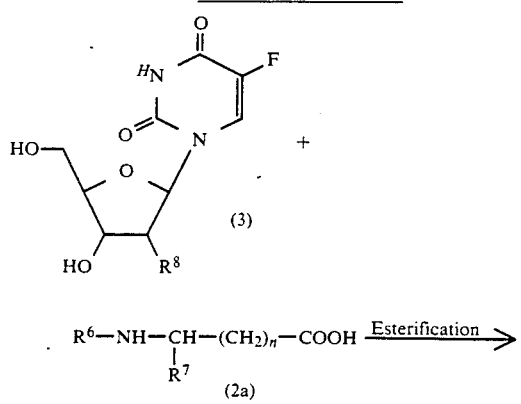

<Reaction scheme A>

-continued

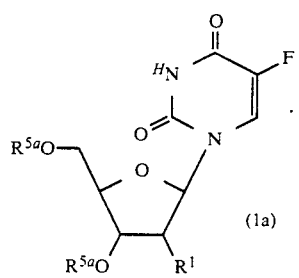

wherein $R^6$, $R^7$ and n have the same meanings as defined above, $R^1$ represents a hydrogen atom or $OR^{5a}$, $R^8$ represents a hydrogen atom or OH group and $R^{5a}$ represents a group represented by the formula (2).

That is, 5-fluorouridine (3a) (a compound wherein $R^8$ in the formula (3) represents OH group) or 2'-deoxy-5-fluorouridine (3b) (a compound wherein $R^8$ in the formula (3) represents a hydrogen atom) is reacted with a compound (2a) by an ester condensation reaction in a suitable solvent in the pesence of a base and a condensing agent to obtain the compound (1a) of the present invention.

As the solvent to be used at this time, it is not limited so long as it does not affect to the reaction, and more specifically it may be mentioned dichloromethane, chloroform, dimethylformamide, dimethylacetamide, dimethylsulfoxide, tetrahydrofuran and acetonitrile.

As the base, there may be used a tertiary amine such as trialkylamine, pyridine, lutidine and 4-(N,N-dimethylamino)pyridine with alone or in combination thereof.

As the condensing agent, there may be used p-toluenesulfonyl chloride, triisopropylbenzenesulfonyl chloride, methanesulfonyl chloride, dicyclohexylcarbodiimide, thionyl chloride, phosphorus oxychloride and N-hydroxysuccinimide.

Amounts of each compound in the reaction are 2 to 6 moles of the compound (2a) and 2 to 8 moles of the base and the condensing agent based on one mole of the compound (3). The reaction temperature is generally under ice-cooling to room temperature and the reaction time is generally 1 hour to 120 hours.

Also, the compound (1b) of the present invention wherein $R^1$ in the formula (1) is OH group and $R^2$ and $R^3$ of the same are both the groups represented by the formula (2), and the compound (1b') of the same wherein $R^2$ and $R^3$ are both hydrogen atoms and $R^5$ is the group represented by the formula (2) can be prepared by using, for example, 5-fluorouridine (3a) as a starting material, following the reaction scheme B shown below.

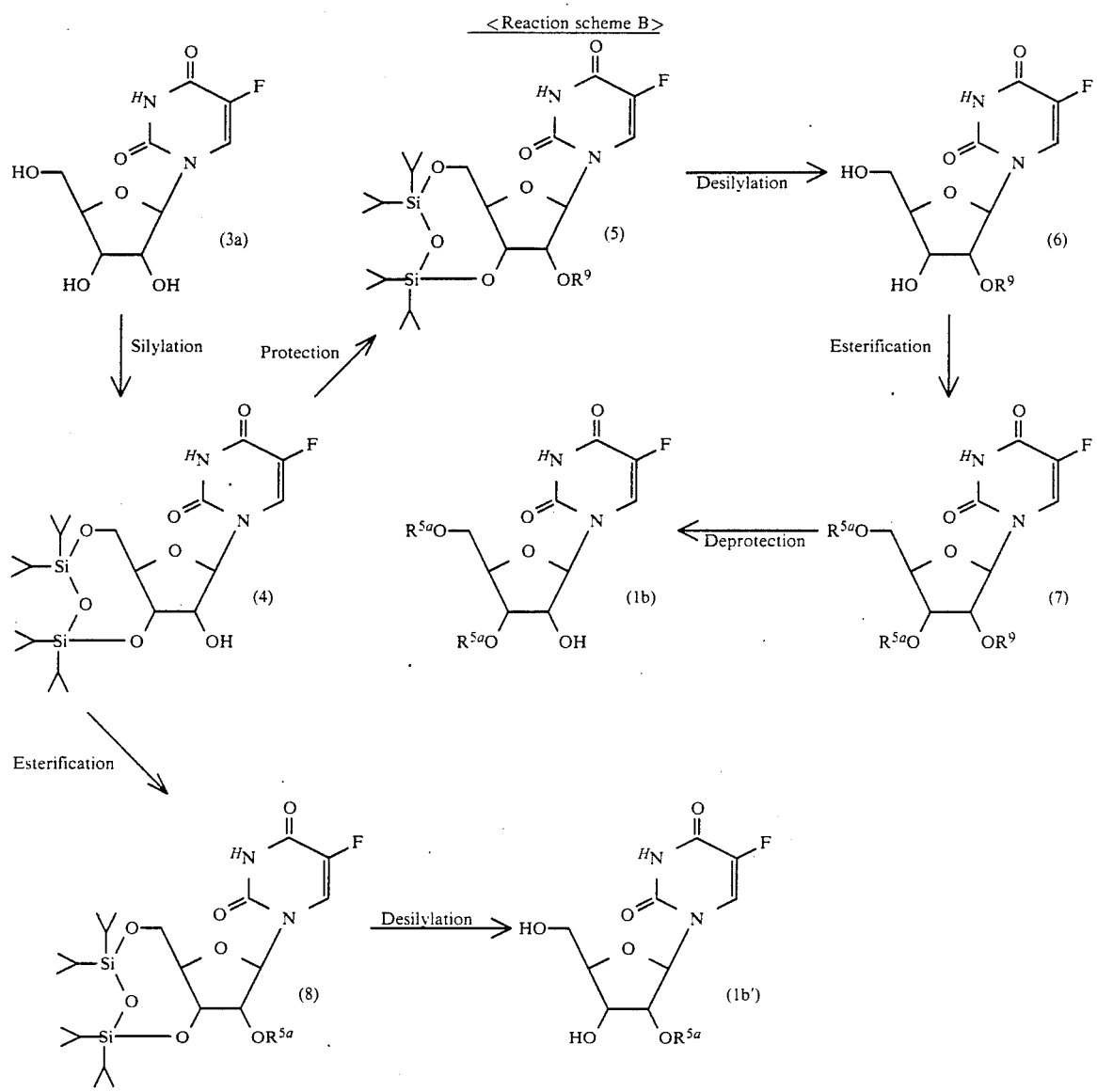

<Reaction scheme B> wherein $R^{5a}$ has the same meaning as defined above, and $R^9$ represents a protective group.

That is, 5-fluorouridine (3a) is reacted with 1,3-dichlorotetraisopropyldisiloxane to give a compound (4), and then a protective group introducing reaction is carried out to give a compound (5) wherein a protective group is introduced at the 2' position. The compound (5) is then applied to a desilylation reaction to give a compound (6), and then the compound (6) is subjected to an ester condensation reaction with the compound (2a) in the same manner as in the reaction scheme A to give a compound (7). When the compound (7) is applied to a deprotection reaction, the compound (1b) of the present invention can be produced.

In the above protective group introducing reaction, as the protective group represented by $R^9$, there may be mentioned, for example, 2-tetrahydrofuranyl group, 2-tetrahydropyranyl group and 2-methoxy-2-methylethyl group. Said reaction can be carried out in a suitable solvent or in the absence of a solvent by using an acid catalyst. As the reaction solvent, it is not limited so long as it does not affect the reaction and more specifically, dioxane, tetrahydrofuran, benzene, toluene, dichloromethane, chloroform, dimethylformamide, dimethylacetamide, dimethylsulfoxide and acetonitrile can be used. As the acid catalyst, hydrogen chloride, sulfuric acid, nitric acid, phosphorus oxychloride, p-toluenesulfonic acid and pyridinium p-toluenesulfonate can be used. The reaction temperature is not particularly limited, but generally under ice-cooling to room temperature, and the reaction time is generally 0.5 hour to 48 hours. Also, the ester condensation reaction can be carried out in the same manner as shown in the above reaction scheme A. However, it is preferred to use 2 to 4 moles of the compound (2a), 2 to 6 moles of the base and 2 to 6 moles of the condensing agent based on one mole of the compound (6) and the reaction time is made 1 hour to 72 hours.

Further, the above deprotecting reaction can be carried out by the conventional method in a suitable solvent by using an acid catalyst. The solvent to be used at this time is not particularly limited so long as it does not affect the reaction, and may include, for example, methanol, ethanol, isopropyl alcohol, dichloromethane and chloroform. These solvents may be used singly or in combination with water. As the acid catalyst, there may be mentioned hydrochloric acid, sulfuric acid, acetic acid and trifluoroacetic acid. The reaction temperature is not particularly limited, but generally under ice-cooling to room temperature and the reaction time is generally 10 minutes to 5 hours..

Also, the compound (1b') of the present invention can be prepared by applying the compound (4) to the ester condensation reaction with the compound (2a) and then subjecting it to a desilylation reaction.

The above ester condensation reaction can be carried out in the same manner as in the above reaction scheme A. However, it is preferred to use 1 to 2 moles of the compound (2a), 1 to 3 moles of the base and 1 to 3 moles of the condensing agent based on one mole of the compound (4) and the reaction time is made 1 hour to 72 hours.

The compounds (1b) and (1b') of the present invention are in relation of tautomer with the compounds of the formulae (1ba) and (1b'a), respectively, as shown below, and they present as a mixture thereof.

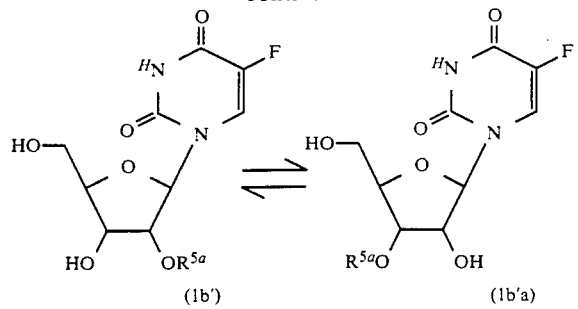

wherein $R^{5a}$ has the same meaning as defined above.

Also, in the formula (1), the compound (1c) of the present invention wherein $R^3$ is a hydrogen atom and $R^2$ and $R^5$ are the groups represented by the formula (2) can be prepared according to the following reaction scheme C by using, for example, 5-fluorouridine (3a) as a starting material.

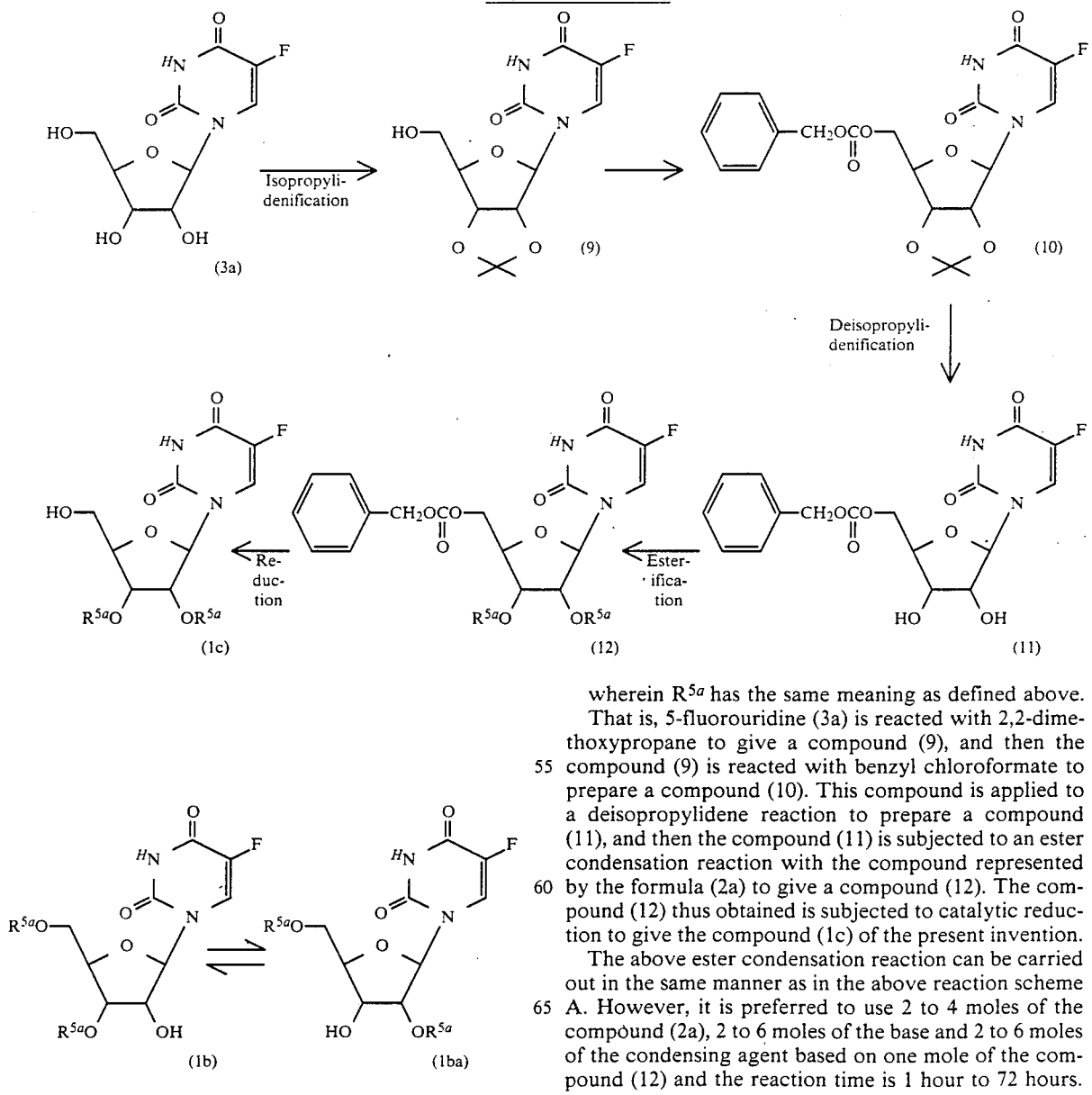

wherein $R^{5a}$ has the same meaning as defined above.

That is, 5-fluorouridine (3a) is reacted with 2,2-dimethoxypropane to give a compound (9), and then the compound (9) is reacted with benzyl chloroformate to prepare a compound (10). This compound is applied to a deisopropylidene reaction to prepare a compound (11), and then the compound (11) is subjected to an ester condensation reaction with the compound represented by the formula (2a) to give a compound (12). The compound (12) thus obtained is subjected to catalytic reduction to give the compound (1c) of the present invention.

The above ester condensation reaction can be carried out in the same manner as in the above reaction scheme A. However, it is preferred to use 2 to 4 moles of the compound (2a), 2 to 6 moles of the base and 2 to 6 moles of the condensing agent based on one mole of the compound (12) and the reaction time is 1 hour to 72 hours.

Also, in the formula (1), the compounds (1d) and (1d') of the present invention wherein $R^1$ is a hydrogen atom and either one of $R^2$ and $R^3$ is a group represented by the formula (2) and the other is a hydrogen atom can be prepared according to the following reaction scheme D by using, for example, 2'-deoxy-5-fluorouridine (3b) as a starting material.

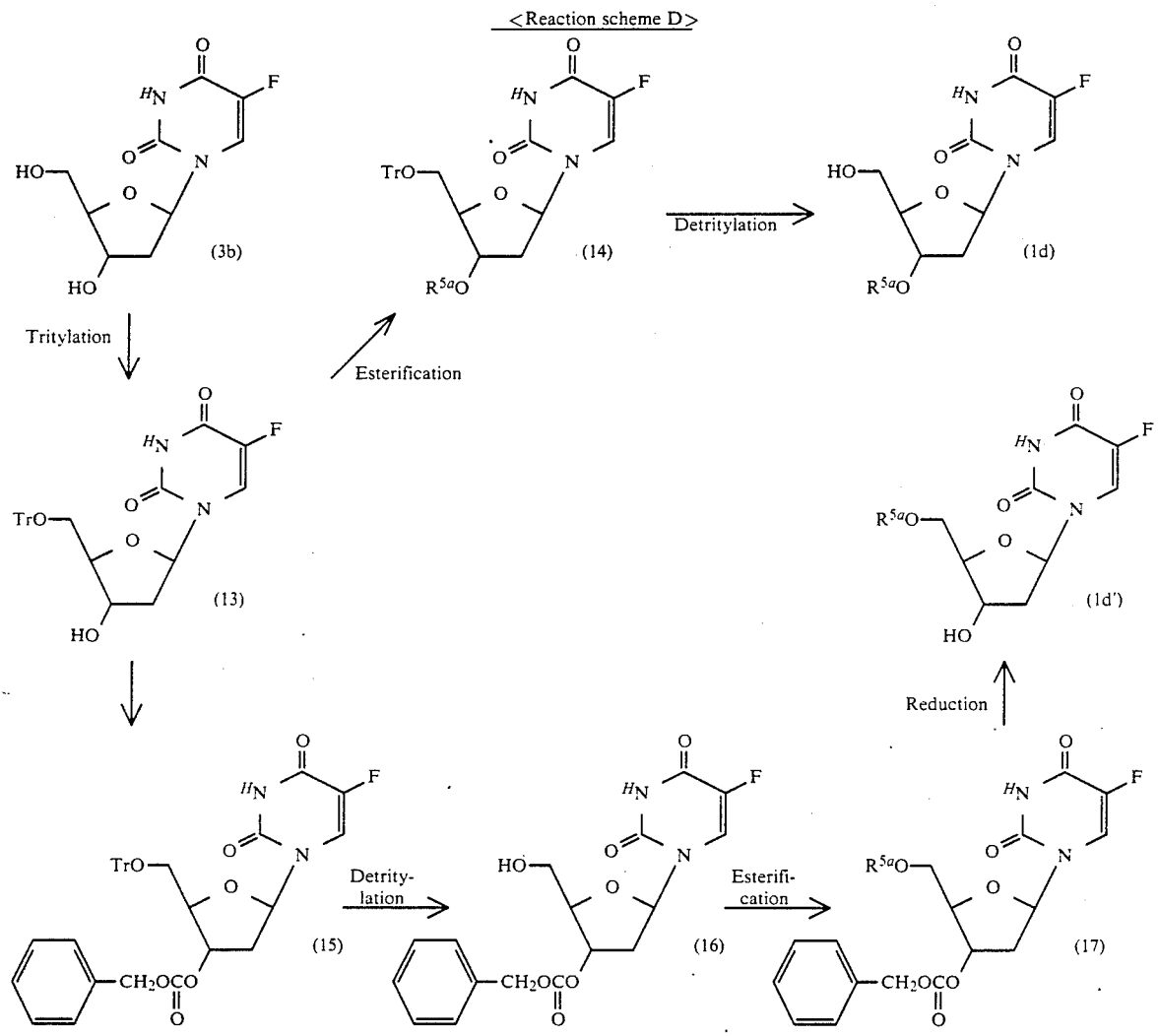

wherein $R^{5a}$ has the same meaning as defined above and Tr represents a triphenylmethyl group.

That is, 2'-deoxy-5-fluorouridine (3b) is reacted with triphenylmethyl chloride to give a compound (13), and the resulting compound (13) is subjected to an ester condensation reaction with the compound represented by the formula (2a) to give a compound (14). The resulting compound (14) is applied to a detritylation reaction to prepare the compound (1d) of the present invention.

The above ester condensation reaction can be carried out in the same manner as in the above reaction scheme A. However, it is preferred to use 1 to 2 moles of the compound (2a), 1 to 3 moles of the base and 1 to 3 moles of the condensing agent based on one mole of the compound (13) and the reaction time is made 1 hour to 72 hours.

Also, the compound (1d') of the present invention can be prepared by procedures that the compound (13) is reacted with benzyl chloroformate to give a compound (15), and the compound (15) is subjected to a detritylation reaction and the resulting compound (16) is subjected to ester condensation reaction with the compound represented by the formula (2a) to give a compound (17) and then the compound (17) is subjected to an catalytic reduction.

The above ester condensation reaction can be carried out in the same manner as in the above reaction scheme C.

The 1-carbamoyl-5-fluorouracil derivatives represented by the formula (1) of the present invention can be prepared by various methods. Examples thereof are shown below, but the present invention is not limited by these methods.

<Reaction scheme E>

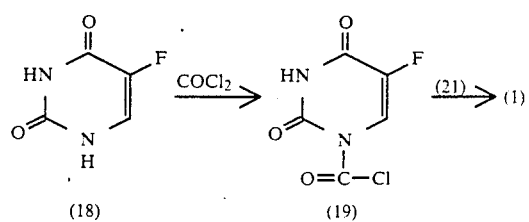

-continued

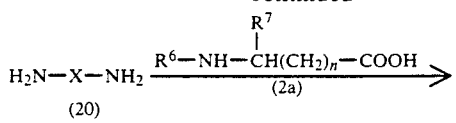
(20)

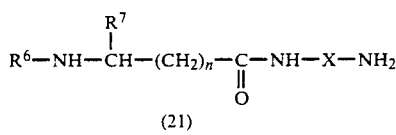
(21)

<Reaction scheme F>

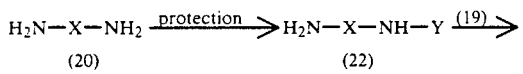

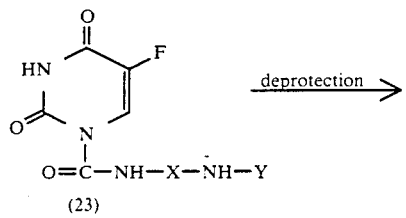
(23)

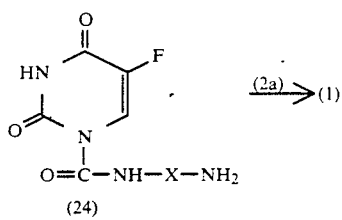
(24)

As shown in the reaction scheme E, with 5-fluorouracil (18) is reacted phosgene (COCl$_2$) to give 1-chlorocarbonyl-5-fluorouracil (19) (see Japanese Provisional Patent Publication No. 151181/1987). With this compound (19) is reacted a compound (21) which can be obtained by dehydration condensation of the compound (20) with the compound (2a) to give the compound (1) of the present invention (wherein X, R$^6$, R$^7$ and n have the same meanings as defined above.). The reaction between 5-fluorouracil (18) and phosgene is generally carried out by dissolving 5-fluorouracil (18) in an organic base such as pyridine, triethylamine and methylmorpholine and while cooling at around $-10°$ to $0°$ C., blowing phosgene therein with an amount equal to or less than that of 5-fluorouracil. A solvent to be used in this reaction is not particularly limited so long it does not affect the reaction and includes, in addition to the above organic base, DMF, DMSO and acetonitrile, etc. These solvents may be used in combination with the above organic base. The reaction of the resulting compound (19) with the compound (21) can be carried out as follows. To the compound (19) obtained in the above reaction without isolation was added dropwise gradually the compound (21) dissolved generally in the same solvent used in the preparation of the compound (19) under cooling at $0°$ C. or lower, preferably $-10°$ to $20°$ C. Further, the reaction is carried out under cooling at $0°$ C. or lower for 1 to 2 hours, and then returning the temperature to room temperature to give the compound (1).

The compound (21) can be prepared by subjecting the compound (20) and the compound (2a) to dehydration condensation in a suitable solvent in the presence of a base and a condensing agent.

As the solvent to be used at this time, it is not limited so long as not affecting the reaction, but more specifically, there may be mentioned dichloromethane, chloroform, dimethylformamide, dimethylacetamide, dimethylsulfoxide, tetrahydrofuran and acetonitrile.

As the base, there may be used a tertiary amine such as trialkylamine, pyridine, picoline, lutidine and 4-(N,N-dimethylamino)pyridine alone or in combination thereof.

As the condensing agent, there may be used dicyclohexylcarbodiimide, thionyl chloride, phosphorus oxychloride and N-hydroxysuccinimide.

Regarding amounts of each compound used in the reaction, the compound (21) can be obtained by reacting the compound (20), the compound (2a), the condensing agent and the base with equal molar ratio, but preferably equal moles of the condensing agent, 2 to 5 moles of the compound (20) and the base based on one mole of the compound (2a) are employed. The reaction temperature is generally under ice-cooling to room temperature and the reaction time is generally 1 hour to 24 hours.

The compound represented by the formula (1) can be also prepared by the route shown by the reaction scheme F. That is, by using a diamine compound (20), a compound (22) in which only one of the amino groups is protected by a usual protective group for the amino group such as t-butoxycarbonyl group is prepared by the well known conventional method (wherein Y represents a protective group). Subsequently, the compound (22) is reacted with the compound (19) under the same conditions as mentioned above, a compound (23) can be obtained (wherein Y has the same meaning as defined above). The compound (23) is deprotected by the well known conventional method to give a compound (24). The compound (24) thus obtained and the compound (2a) are subjected to dehydration condensation in the same conditions as mentioned above to give the title compound (1).

EXAMPLES

In the following, the compounds of the present invention will be explained in more detail by referring to Reference examples, Examples and Pharmacological test examples.

However, the present invention is not limited by these Examples.

REFERENCE EXAMPLE 1

Preparation of N-(2-n-propyl-n-pentanoyl)glycine (2a)

In 63 ml of water was dissolved 6.93 g of glycine, and under ice-cooling, 15 g of 2-n-propyl-n-pentanoyl chloride and 13 ml of a 36% sodium hydroxide solution were alternately added dropwise. After completion of the dropwise addition, the mixture was stirred at room temperature for 3 hours to conduct the reaction, adjusted a pH thereof to about 2 with a 1 N hydrochloric acid, and precipitated crystals were collected by filtration. The crystals were dissolved in ethyl acetate, washed with a saturated saline solution and then dried over anhydrous magnesium sulfate. Crystals obtained by condensing the solvent under reduced pressure were recrystallized from hexane-ethyl acetate to give 10.9 g (Yield: 59%) of the title compound as colorless needle crystals.

REFERENCE EXAMPLE 2

Preparation of 3',5'-O-(tetraisopropyldisiloxane-1,3-diyl)-5-fluorouridine (4)

In 300 ml of pyridine was dissolved 10 g of 5-fluorouridine and, under ice-cooling and stirring, 13.2 g of 1,3-dichlorotetraisopropyldisiloxane was added dropwise. After completion of the dropwise addition, the mixture was stirred at room temperature for 6 hours to conduct the reaction, and the solvent was removed under reduced pressure. The resulting residue was dissolved in 220 ml of chloroform, and washed successively with water, 1 N-hydrochloric acid and water. The chloroform layer was dried over anhydrous magensium sulfate, condensed under reduced pressure and the residue obtained was applied to silica gel column chromatography to obtain 12.1 g (Yield: 54%) of the title compound.

NMR (CDCl$_3$) δ: 9.87 (1H, bs), 7.91 (1H, d), 5.75 (1H, d), 4.35–4.15 (4H. m), 4.0 (1H, dd), 3.69 (1H, bd), 1.17–0.97 (28H, m).

REFERENCE EXAMPLE 3

Preparation of 3',5'-O-(tetraisopropyldisiloxane-1,3-diyl)-2'-O-(2-tetrahydropyranyl)-5-fluorouridine (5)

In 5 ml of methylene chloride were dissolved 0.5 g of 3',5'-O-(tetraisopropyldisiloxane-1,3-diyl)-5-fluorouridine and 0.17 g of 2,3-dihydropyran, and after adding 50 mg of pyridinium p-toluenesulfonate, the mixture was stirred at room temperature for 3.5 hours to conduct the reaction. After completion of the reaction, 5 ml of ether was added to the reaction mixture and the mixture was washed with water. The organic layer was dried over anhydrous magnesium sulfate and condensed under reduced pressure, and the obtained residue was applied to silica gel column chromatography to give 0.46 g (Yield: 79%) of the title compound.

Melting point: 82° to 85° C.
CI-Mass (m/z): 589 (M$^+$+1), 505.

REFERENCE EXAMPLE 4

Preparation of 2'-O-(2-tetrahydropyranyl)-5-fluorouridine (6)

In 100 ml of tetrahydrofuran was dissolved 12.4 g of 3',5'-O-(tetraisopropyldisiloxane-1,3-diyl)-2'-0-(2-tetrahydropyranyl)-5-fluorouridine, and after 21 ml of 1 M tetrahydrobutyl ammonium fluoride-tetrahydrofuran solution was added thereto under ice-cooling and stirring, the mixture was stirred at room temperature for 40 minutes to conduct the reaction. To the mixture was added 3.7 g of sodium hydrogen carbonate, and after stirring at room temperature for 30 minutes, the filtrate was condensed under reduced pressure. The obtained residue was applied to silica gel column chromatography to give the title compouds as two kinds of stereoisomers.

An isomer having a larger Rf value (0.19) according to the thin layer chromatographic analysis (CHCl$_3$/MeOH=9/1)
Yield: 42%
Melting point: 93° to 96° C.
CI-Mass (m/z): 347 (M$^+$+1), 263.
An isomer having a smaller Rf value (0.14)
Yield: 52%
Melting point: 173° to 175° C.
CI-Mass (m/z): 347 (M$^+$+1), 263.

REFERENCE EXAMPLE 5

Preparation of 3',5'-bis-O-[N-(2-n-propyl-n-pentanoyl)-glycyl]2'-O-(2-tetrahydropyranyl)-5-fluorouridine (7)

To a suspension in which 0.64 g of N-(2-n-propyl-n-pentanoyl)glycine was suspended in 35 ml of methylene chloride was added under ice-cooling and stirring 0.65 g of dicyclohexylcarbodiimide, and then the mixture was stirred under ice-cooling for 15 minutes. Then, 0.55 g of 2'-O-(2-tetrahydropyranyl)-5-fluorouridine (an isomer having a smaller Rf value obtained in Reference example 4), 0.38 g of triethylamine and 0.19 g of 4-(N,N-dimethylamino)pyridine were added to the mixture and the reaction was carried out at room temperature for 1.5 hours. After allowed to stand overnight at room temperature, the reaction mixture was condensed under reduced pressure, and 20 ml of ethyl acetate was added to the obtained residue and insolubles were filtered off. The filtrate was condensed under reduced pressure and the obtained residue was applied to silica gel column chromatography to give 0.19 g (Yield: 17%) of the title compound.

NMR (CDCl$_3$) δ: 9.38 (1H, bs), 7.44 (1H, d), 6.3 (1H, t), 6.26 (1H, t), 5.75 (1H, d), 5.28 (1H, ddd), 4.6–4.3 (5H, m), 4.24–4.05 (4H. m), 3.78–3.65 (1H, m), 3.53–3.4 (1H, m), 2.27–2.1 (2H, m), 1.9–1.1 (22H, m), 0.89 (12H, tx4).

REFERENCE EXAMPLE 6

Preparation of 2',3'-O-isopropylidene-5-fluorouridine (9)

In 750 ml of acetone were added 15 g of 5-fluorouridine, 7.5 ml of 2,2-dimethoxypropane and 1.1 g of p-toluenesulfonic acid monohydrate, and the mixture was reacted at room temperature for 4.5 hours under stirring. After allowed to stand overnight at room temperature, 5 g of sodium hydrogen carbonate was added to the reaction mixture and the mixture was stirred at room temperature for 2.5 hours. After insolubles were filtered off, the filtrate was condensed under reduced pressure, and the obtained crystals were recrystallized from ethanol to give 15.7 g (Yield: 84%) of the title compound as colorless needle crystals.

REFERENCE EXAMPLE 7

Preparation of 5'-O-benzyloxycarbonyl-2',3'-O-isopropylidene-5-fluorouridine (10)

In 45 ml of methylene chloride were dissolved 0.68 g of 2',3'-O-isopropylidene-5-fluorouridine and 0.3 g of 4-(N,N-dimethylamino)pyridine, and after 0.35 ml of benzyl chloroformate was added dropwise under ice-cooling and stirring, the mixture was reacted at room temperature for 9.5 hours under stirring. After allowed to stand overnight at room temperature, the residue obtained by condensing the reaction mixture under reduced pressure was applied to silica gel column chromatography to give 0.75 g (Yield: 76%) of the title compound.

NMR (CDCl$_3$) δ: 8.25 (1H, bd), 7.48 (1H, d), 5.85 (1H, d), 5.18 (2H, s), 4.87–4.77 (2H, m), 4.45–4.35 (3H, m), 1.58 (3H, s), 1.35 (3H, s).

REFERENCE EXAMPLE 8

Preparation of 5'-O-benzyloxycarbonyl-5-fluorouridine (11)

In 3.1 ml of a 90% trifluoroacetic acid solution was dissolved 0.71 g of 5'-O-benzyloxycarbonyl-2',3'-O-isopropylidene-5-fluorouridine under ice-cooling and stirring, and the solution was stirred at room temperature for one hour. The residue obtained by condensing the reaction mixture under reduced pressure was applied to silica gel column chromatography to give 0.54 g (Yield: 84%) of the title compound.

Melting point: 66° C. to 68° C.
CI-Mass (m/z) 397 ($M^+ + 1$), 379, 267.

REFERENCE EXAMPLE 9

Preparation of 5'-O-benzyloxycarbonyl-2',3'-bis-O-[N-(2-n-propyl-n-pentanoyl)glycyl-5-fluorouridine (12)

To a suspension in which 0.5 g of N-(2-n-propyl-n-pentanoyl)glycine was suspended in 30 ml of methylene chloride was added 0.51 g of dicyclohexylcarbodiimide under ice-cooling and stirring, and then the mixture was stirred under ice-cooling for 10 minutes. Then, 0.54 g of 5'-O-benzyloxycarbonyl-5-fluorouridine, 0.3 g of triethylamine and 0.15 g of 4-(N,N-dimethylamino)pyridine were added to the mixture, and the mixture was reacted at room temperature for 10 hours under stirring. Thereafter, the reaction mixture was treated according to the same method as in Reference example 5 to give 0.62 g (Yield: 60%) of the title compound.

Melting point: 75° to 77° C.
CI-Mass (m/z) 763 ($M^+ + 1$), 632.

REFERENCE EXAMPLE 10

Preparation of 2'-deoxy-5'-O-trityl-5-fluorouridine (13)

In 2.5 ml of pyridine were dissolved 0.25 g of 2'-deoxy-5-fluorouridine and 0.34 g of trityl chloride, and the solution was reacted at 60° C. for 4 hours under stirring. After completion of the reaction, the reaction mixture was poured into 80 ml of ice-cold water and precipitated crystals were collected by filtration. These crystals were dissolved in 30 ml of ethyl acetate, washed with saturated saline solution, dried over anhydrous magnesium sulfate and condensed under reduced pressure. The residue obtained was applied to silica gel column chromatography to give 0.28 g (Yield: 56%) of the title compound.

REFERENCE EXAMPLE 11

Preparation of 2'-deoxy-3'-O-[N-(2-n-propyl-n-pentanoyl)-glycyl]-5'-O-trityl-5-fluorouridine (14)

To a suspension in which 0.11 g of N-(2-n-propyl-n-pentanoyl)glycine was suspended in 15 ml of methylene chloride was added 0.11 g of dicyclohexylcarbodiimide under ice-cooling and stirring, and then the mixture was stirred under ice-cooling for one hour. Then, 0.27 g of 2'-deoxy-5'-O-trityl-5-fluorouridine, 70 mg of triethylamine and 34 mg of 4-(N,N-dimethylamino)pyridine were added to the mixture, and the mixture was reacted at room temperature for two days under stirring. Thereafter, the reaction mixture was treated according to the same method as in Reference example 5 to give 0.26 g (Yield: 70%) of the title compound.

NMR (CDCl$_3$) δ: 8.51 (1H, d), 7.89 (1H, d), 7.57-7.21 (15H, m), 6.29 (1H, dd), 5.9 (1H, t), 5.52 (1H, dd), 4.18 (1H, ddd), 4.07 (2H, d), 3.55 (1H, dd), 3.39 (1H, dd), 2.59 (1H, ddd), 2.35 (1H, ddd), 2.23-2.05 (1H, m), 1.73-1.19 (8H, m), 0.9 (6H, tx2).

REFERENCE EXAMPLE 12

Preparation of N-[N-(2-n-propyl-n-pentanoyl)glycyl]hexamethylenediamine

To a suspension in which 2.01 g of N-(2-n-propyl-n-pentanoyl)glycine was suspended in 30 ml of methylene chloride which was cooled in an ice-salt bath was added 2.06 g (10 mmole) of dicyclohexylcarbodiimide in the state of crystal as such, and the mixture was stirred for about 30 minutes while cooling. The suspension thus prepared was added to a solution in which 2.32 g (20 mmole) of hexamethylenediamine and 2.02 g (20 mmole) of triethylamine dissolved in 20 ml of methylene chloride. the mixture was stirred under cooling by ice-cold water for about 2 hours and then at room temperature for about 3 hours, and then allowed to stand overnight. Precipitated dicyclohexylurea was filtered off and the resulting filtrate having red-brownish color was washed with 50 ml of water three times. The methylene chloride solution thus obtained was dried over anhydrous sodium sulfate, and then condensed under reduced pressure to give red-brownish oily product. This material was purified by silica gel (Wako gel C-200, trade name, produced by Wako Jun-yaku Co.) column chromatography using a developing solution comprising a mixed solvent of methanol: 28% aqueous ammonia=9:1 to give 1.94 g (Yield: 68%) of the title compound as red-brownish oily product.

CI-MS (m/z): 300 ($M^+ + 1$).
$^1$H-NMR (CDCl$_3$) δ (ppm): 0.90 (6H, t), 1.11-1.78 (16H, b,m), 2.15 (1H, m), 2.68 (2H, t), 3.25 (2H, m), 3.92 (2H, d), 6.60 (2H, b).

EXAMPLE 1

Preparation of 2',3',5'-tris-O-[N-(2-n-propyl-n-pentanoyl)-glycyl]-5-fluorouridine (1a)

To a suspension in which 8.86 g of N-(2-n-propyl-n-pentanoyl)glycine was suspended in 380 ml of methylene chloride was added 9.01 g of dicyclohexylcarbodiimide under ice-cooling and stirring, and then the mixture was stirred under ice-cooling for 50 minutes. Then, 1.63 g of 5-fluorouridine, 4.45 g of triethylamine and 1.63 g of 4-(N,N-dimethylamino)pyridine were added to the mixture, and the mixture was stirred at room temperature for 4 days. Thereafter, the reaction mixture was treated according to the same method as in Reference example 5 to give 4.62 g (Yield: 43%) of the title compound.

Melting point: 94° to 97° C.
Elemental analysis value (as $C_{39}H_{62}FN_5O_{12}\cdot\frac{1}{2}H_2O$) Calcd. (%) C: 57.06, H: 7.74, N: 8.53; Found. (%) C: 57.06, H: 7.72, N: 8.59.

EXAMPLE 2

Preparation of 2',3',5'-tris-O-(benzoyl-DL-alanyl)-5-fluorouridine (1a)

In the same manner as in Example 1, the title compound was obtained with a yield of 10%.

Melting point: 87° to 89° C.
FD-Mass (m/z): 788 ($M^+ + 1$), 595.

EXAMPLE 3

Preparation of
2'-deoxy-3',5'-bis-O-[N-(2-n-propyl-n-pentanoyl)-glycyl]-5-fluorouridine (1a)

To a suspension in which 2.04 g of N-(2-n-propyl-n-pentanoyl)glycine was suspended in 110 ml of methylene chloride was added 2.09 g of dicyclohexylcarbodiimide under ice-cooling and stirring, and the mixture was stirred under ice-cooling for 20 minutes. Then, 1.25 g of 2'-deoxy-5-fluorouridine, 1.23 g of triethylamine and 0.62 g of 4-(N,N-dimethylamino)pyridine were added to the mixture and the mixture was reacted at room temperature for one day under stirring. Thereafter, crystals obtained by processing according to the method in Reference example 5 were recrystallized from acetone-water to give 1.38 g (Yield: 44%) of the title compound as colorless needle crystals.
Melting point: 191° to 192° C.
CI-Mass (m/z): 613 (M++1), 412.

EXAMPLE 4

Preparation of
3',5'-bis-O-[N-(2n-propyl-n-pentanoyl)-glycyl]-5-fluorouridine (1b)

In 6 ml of ethanol was dissolved 0.5 g of 3',5'-bis-O-[N-(2-n-propyl-n-pentanoyl)glycyl]-2'-O-(2-tetrahydropyranyl)-5-fluorouridine, and after adding 18 mg of pyridinium p-toluenesulfonate at room temperature under stirring, the mixtuer was stirred at 55° C. for 3.5 hours. The residue obtained by condensing the reaction mixture under reduced pressure was applied to silica gel column chromatography to give 0.34 g (Yield: 77%) of the title compound.
Melting point: 91° to 94° C.
Elemental analysis value (as $C_{29}H_{45}FN_4O_{10}.\frac{1}{4}H_2O$) Calcd. (%) C: 55.01, H: 7.24, N: 8.85, Found. (%) C: 54.92, H: 7.03, N: 8.68.

EXAMPLE 5

Preparation of
2',3'-bis-O-[N-(2-n-propyl-n-pentanoyl)-glycyl]-5-fluorouridine (1c)

After dissolving 0.62 g of 5'-O-benzyloxycarbonyl-2',3'-bis-O-[N-(2-n-propyl-n-pentanoyl)glycyl]-5-fluorouridine in 25 ml of ethanol, 0.2 g of 5% palladium carbon was added to the solution and the mixture was stirred under hydrogen stream, at room temperature and atmospheric pressure for 50 minutes. After the catalyst was filtered off, the residue obtained by condensing the reaction mixture under reduced pressure was applied to silica gel column chromatography to give 0.36 g (Yield: 68%) of the title compound.
Melting point: 99° to 102° C.
Elemental analysis value (as $C_{29}H_{45}FN_4O_{10}.H_2O$) Calcd. (%) C: 53.85, H: 7.03, N: 8.66 Found. (%) C: 53.72, H: 7.20, N: 8.38.

EXAMPLE 6

Preparation of
2'-deoxy-3'-O-[N-(2-n-propyl-n-pentanoyl)-glycyl-5-fluorouridine (1d)

In 1.7 ml of a 50% trifluoroacetic acid solution was dissolved 0.24 g of 2'-deoxy-3'-O-[N-(2-n-propyl-n-pentanoyl)-glycyl]-5'-O-trityl-5-fluorouridine, and under ice-cooling, the solution was stirred for 15 minutes. The residue obtained by condensing the reaction mixture under reduced pressure was applied to silica gel column chromatography to give 0.12 g (Yield: 78%) of the title compound.
NMR (CDCl$_3$-DMSO-d$_6$) δ: 11.85 (1H, d), 8.27 (1H, t), 8.22 (1H, d), 6.2 (1H, dd), 5.4–5.23 (2H, m), 4.09–4.0 (1H, m), 3.85 (2H, d), 3.68 (2H, s), 2.35–2.13 (3H, m), 1.6–1.12 (8H, m), 0.87 (6H, tx2).

EXAMPLE 7

Preparation of
1-[6-[N-(2-n-propyl-n-pentanoyl)glycyl]amino-n-hexylcarbamoyl]-5-fluorouracil A solution of 6.69 g (51.4 mmole) of 5-fluorouracil dissolved in 130 ml of pyridine was cooled to −5° C. or so by an ice-salt bath, and 4.58 g (46.3 mmole) of phosgene formed by decomposing trichloromethyl chloroformate (TCF) with activated charcoal was blown therein to conduct the reaction. A yellowish crystals-suspended liquor thus prepared was stirred for one hour under cooling. This suspension was cooled to −20° C. or so by using a dry ice-ethanol bath, and added dropwise a solution comprising 10.23 g (34.16 mmole) of N-[N-(2-n-propyl-n-pentanoyl)-glycyl]hexamethylenediamine synthesized by the method shown in Reference example 12 and 9.37 g (92.6 mmole) of triethylamine dissolved in 50 ml pyridine over about 40 minutes. After completion of the dropwise addition, the mixture was continued to stirring at −15° C. or so for about one hour and allowed to stand overnight at room temperature. Insolubles were filtered off, and the resulting red filtrate was condensed under reduced pressure. Toluene was added to the residue and the mixture was again condensed under reduced pressure to substantially completely remove pyridine. The residue thus obtained was dissolved in 300 ml of chloroform and washed with 100 ml of water three times. After the chloroform layer was dried over anhydrous sodium sulfate, it was condensed under reduced pressure. A red-brownish viscous material was obtained and was separated by silica gel column chromatography using a mixed solvent of toluene: ethyl acetate: methanol=4:2:1 as a developing solution to give 15.83 g of pale orange crystals. This crystal can be confirmed to be the title compound by analysis. Yield: 101.7%.

These crystals were suspended in 120 ml of methanol, stirred and then filtered to give 9.18 g of substantially colorless crystals.
Elemental analysis value (as $C_{21}H_{34}FN_5O_5.1/2H_2O$) Calcd. (%) C: 54.29, H: 7.59, N: 15.08, Found. (%) C: 54.13, H: 7.32, N: 14.99.
Melting point: 111.0° to 111.5° C.

EXAMPLE 8

Preparation of
1-[5-[N-(2-n-propyl-n-pentanoyl)glycyl]-amino-n-pentylcarbamoyl]-5-fluorouracil In a solution of 1.09 g (8.42 mmole) of 5-fluorouracil dissolved in 30 ml of pyridine was blown 0.75 g (7.58 mmole) of phosgene in the same manner as described in Example 7 to conduct the reaction. A yellowish crystals-suspended liquor thus prepared was stirred for one hour under cooling. Under substantially the same conditions as in Example 7, to this suspension was added dropwise a solution comprising 1.93 g (6.76 mmole) of N-[N-(2-n-propyl-n-pentanoyl)glycyl]pentamethylenediamine synthesized by reacting pentamethylenediamine and N-(2-propyl-n-pentanoyl)glycine under substantially the same conditions described in Reference example 12 and 1.53 g (15.16 mmole) of triethylamine dissolved in 20 ml pyridine to conduct the reaction. After treating the reaction mixture in the same manner as described in Example 7, by using the same developing solvent as described in Example 7, fractions which seem to be the title compound were collected. 1.15 g (Yield: 38.5%) of pale yellow crystals were obtained. A part of the crystals was purified again by using silica gel column chromatography with the same developing solvent to give pure 1-[5-[N-(2-n-propyl-n-pentanoyl)glycyl]amino-n-pentylcarbamoyl]-5-fluorouracil as colorless crystals.

Elemental analysis value (as $C_{20}H_{32}FN_5O_5$) Calcd. (%) C: 54.41, H: 7.31, N: 15.86; Found. (%) C: 54.31, H: 7.26, N: 15.60.

Melting point: 117.0° to 118.0° C.

EXAMPLE 9

Preparation of
1-[4-[N-(2-n-propyl-n-pentanoyl)glycyl-aminocyclohexylcarbamoyl]-5-fluorouracil The reaction was carried out in the same manner as in Example 7 except for using 1.77 g (13.6 mmole) of 5-fluorouracil, 2.68 g (8.88 mmole) of 4-amino-1-[N-(2-n-propyl-n-pentanoyl)glycyl] aminocyclohexane, 1.21 g (12.2 mmole) of phosgene and 2.48 g (24.4 mmole) of triethylamine. 3.22 g (Yield: 79.9%) of crude crystals obtained by silica gel column chromatography was recrystallized from 50 ml of acetonitrile to give 1.74 g of the title compound as colorless powdery crystals.

Elemental analysis value (as $C_{21}H_{32}FN_5O_5$) Calcd. (%) C: 55.62, H: 7.11, N: 15.44 Found. (%) C: 55.55, H: 7.24, N: 15.66.

Melting point: 156.6° to 158.5° C.

EXAMPLE 10

Preparation of
1-[12-[N-(2-n-propyl-n-pentanoyl)glycyl]-amino-n-dodecylcarbamoyl]-5-fluorouracil The reaction was carried out in the same manner as in Example 7 except for using 2.42 g (18.6 mmole) of 5-fluorouracil, 3.91 g (10.2 mmole) of N-[N-(2-n-propyl-n-pentanoyl)glycyl]dodecamethylenediamine, 1.66 g (16.8 mmole) of phosgene and 3.40 g (33.6 mmole) of triethylamine. By treating the reaction mixture, 5.81 g of red-brownish crystals were obtained.

These crystals were dispensed by silica gel column chromatography using the same developing solvent as in Example 7 to give 3.03 g (Yield: 55.1%) of the title compound as colorless crystals.

Elemental analysis value (as $C_{27}H_{46}FN_5O_5$) Calcd. (%) C: 60.09, H: 8.59, N: 12.98 Found. (%) C: 60.08, H: 8.77, N: 12.97.

Melting point: 116.0° to 117.5° C.

REFERENCE EXAMPLE 13

Preparation of
N-(t-butoxycarbonyl)hexamethylenediamine

A solution of 27.9 g (240 mmole) of hexamethylenediamine and 24.3 g (240 mmole) of triethylamine dissolved in 400 ml of methylene chloride was cooled with an ice-salt bath and to the solution was added dropwise a solution of 17.46 g (80 mmole) of di-t-butyl dicarbonate dissolved in 100 ml of methylene chloride over about 1.5 hours. After allowed to stand at room temperature overnight, the mixture was further stirred at room temperature for one day. The reaction mixture was washed successively with 300 ml of water once and 100 ml of the same twice. Subsequently, the methylene chloride layer was dried over anhydrous sodium sulfate, and condensed under reduced pressure. When the resulting red-brownish oily product was allowed to stand at room temperature, it gradually crystallized. This crystal was dispensed by silica gel column chromatography using a developing solvent of methanol: 28% aqueous ammonia=19:1 to give 14.05 g (Yield: 81.2%) of a red-brownish liquid.

REFERENCE EXAMPLE 14

Preparation of
1-[6-(t-butoxycarbonylamino)-n-hexylcarbamoyl]-5-fluorouracil

The reaction was carried out in the same manner as in Example 7 except for using 9.06 g (69.6 mmole) of 5-fluorouracil, 6.20 g (62.7 mmole) of phosgene, 12.68 g (125.3 mmole) of triethylamine, and 11.36 g (52.5 mmole) of N-(t-butyoxycarbonyl)hexamethylenediamine synthesized in Reference example 13 in place of N-[N-(2-n-propyl-n-pentanoyl)-glycyl]hexamethylenediamine used in Example 7. The reaction mixture was treated in the same manner as in Example 7 to give 16.06 g (Yield: 91.3%) of pale yellowish crystals. 1 g of this crystals was recrystallized from 15 ml of ethyl acetate to give 0.52 g of colorless needle crystals.

Elemental analysis value (as $C_{16}H_{25}FN_4O_5$) Calcd. (%) C: 51.61, H: 6.77, N: 15.05; Found. (%) C: 51.29, H: 6.77, N: 14.81.

REFERENCE EXAMPLE 15

Preparation of
1-(6-amino-n-hexylcarbamoyl)-5-fluorouracil

In 10 ml of a mixed solution of anhydrous trifluoroacetic acid: water=9:1 was suspended 0.74 g (2 mmole) of 1-[6-(t-butoxycarbonylamino)-n-hexylcarbamoyl]-5-fluorouracil under ice-cooling. When the suspension was stirred under ice-cooling, it was gradually dissolved to form a uniform solution. After stirring about one hour, the mixture was condensed under reduced pressure. To the residue was added 50 ml of toluene, and azeotropically dehydrated by reduced pressure condensation. To the residue was again added 50 ml of toluene, the same procedure as mentioned above was carried out. When about 100 ml of chloroform was added to the residue and allowed to stand overnight, the residue crystallized. Chloroform was removed under reduced pressure and the residue was recrystallized from 20 ml of ethanol. The title compound can be obtained with an amount of 0.29 g (Yield: 37.5%) as a salt of trifluoroacetic acid with a molar ratio of 1:1.

Elemental analysis value (as $C_{13}H_{18}F_4N_4O_5$) Calcd. (%) C: 40.42, H: 4.70, N: 14.50; Found. (%) C: 40.24, H: 4.73, N: 14.22.

EXAMPLE 11

Preparation of
1-[6-[N-(2-nopropyl-n-pentanoyl)glycyl]-amino-n-hexylcarbamoyl-5-fluorouracil In 60 ml of methylene chloride was suspended 4.51 g (22.4 mmole) of N-(2-n-propyl-nopentanoyl)glycine. The suspension was cooled with an ice-salt bath and 4.63 g (22.4 mmole) of dicyclohexylcarbodiimide was added thereto, and the mixture was stirred for one hour while cooling. The suspension thus obtained was added under ice-cold water cooling to a pale yellowish suspension obtained by mixing 4.16 g of triethylamine and 7.23 g (18.7 nmole) of an adduct of 1-(6-amino-n-hexylcarbamoyl)-5-fluorouracil and trifluoroacetic acid with a ratio of 1:1 suspended in 50 ml of DMF. The mixture was stirred under cooling for 2 hours, and at room temperature for further 2 hours, and then allowed to stand at room temperature for 2 days.

The reaction mixture was condensed under reduced pressure and to the resulting red-brownish residue were added 100 ml of chloroform and 50 ml of water. After insolubles were filtered off, liquids were separated and the aqueous layer was extracted with 50 ml of chloroform twice. The extracts were combined with the chloroform layer which can be previously obtained by liquid separation, and the mixture was dried over anhydrous sodium sulfate and condensed under reduced pressure. The residue was applied to silica gel column chromatography using firstly a mixed solvent of chloroform: ethyl acetate=3:1 as a developing solvent and then a mixed solvent of toluene: ethyl acetate: methanol=4:2:0.5 to dispense the title compound. Yellowish glass state crystals were obtained with an amount of 5.79 g (Yield: 68.0%). Since the infrared absorption spectrum of this crystal completely accorded with that of the compound obtained in Example 7, it car be confirmed to be 1-[6-[N-(2-n-propyl-n-pentanoyl)glycyl-]amino-n-hexylcarbamoyl]-5-fluorouracil.

Pharmacological test example 1

To a microwell having 9 holes were planted KB cell with $2 \times 10^4$, respectively, and after 12 hours, the compounds of the present invention obtained in Example 1 and Example 4 and 5-fluorouracil were added (3 well/dose). After cultivating for 5 days, the number of cells were measured and from a cell proliferation inhibiting ratio-concentration curve, 50% cell proliferation inhibiting concentration ($IC_{50}$ value) at which the inhibiting ratio becomes 50% was evaluated. The results are shown in Table 1.

TABLE 1

| Test compound | $IC_{50}$ (nM/ml) |
|---|---|
| Compound of Example 1 | 2.0 |
| Compound of Example 4 | 1.8 |
| 5-Fluorouracil | 17.7 |

Pharmacological test example 2

To a microwell having 9 holes were planted KB cell with $5 \times 10^3$, respectively, and after 24 hours, the compound of the present invention obtained in Example 7 and 5-fluorouracil were added. After cultivating for 5 days, the number of cells were measured and from a cell proliferation inhibiting ratio-concentration curve, 50% cell proliferation inhibiting concentration ($IC_{50}$ value) at which the inhibiting ratio becomes 50% was evaluated. The results are shown in Table 2.

TABLE 2

| Test compound | $IC_{50}$ (M) |
|---|---|
| Compound of Example 7 | $6.6 \times 10^{-7}$ |
| 5-Fluorouracil | $7.5 \times 10^{-7}$ |

Pharmacological test example 3 (acute toxicity)

The compounds of the present invention obtained in Examples 4 and 7 were orally administered to 7 week-old BDF2 female mouse (10 mice per group). After 21 days from the administration, mortality of the mice was judged and $LD_{50}$ value was evaluated from mortality according to the Richfield-Wilcokson method. The results are shown in Table 3.

TABLE 3

| Test compound | $ID_{50}$ (mg/kg) |
|---|---|
| Compound of Example 1 | 5000 or more |
| Compound of Example 4 | 3000 or more |
| Compound of Example 7 | 1000 or more |
| 5-Fluorouracil | 928 |

As can be clearly seen from the above, 5-fluorouridine, 2'-deoxy-5-fluorouridine and 5-fluorouracil derivatives of the present invention have potent antitumor activity and low toxicity as compared with those of 5-fluorouracil.

We claim:

1. A 5-fluorouracil compound represented by the formula (1):

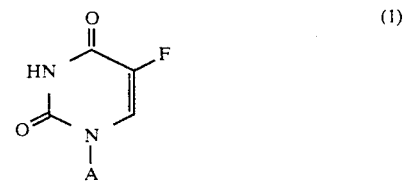

wherein A represents a group represented by

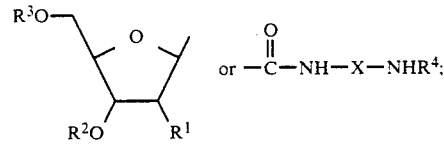

wherein $R^1$ represents a hydrogen atom or $OR^5$ group; $R^2$, $R^3$ and $R^5$ is the same or different and each represents a hydrogen atom or a group represented by the following formula (2):

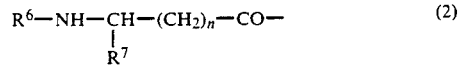

wherein $R^6$ represents an unsubstituted or substituted straight or branched alkanoyl group having 1 to 13 carbon atoms, aralkylcarbonyl group or aroyl group, $R^7$ represents a hydrogen atom, a straight or branched alkyl group having 1 to 13 carbon atoms, a cyclopentyl group, a cyclohexyl group, benzyl, 2-phenethyl, a lower alkenyl group to which a halogen may be substituted, or a phenyl group to which a lower alkyl, a lower alkenyl or a halogen may be substituted, and n is an integer of 0 to 6, provided that when at least one of $R^2$, $R^3$ and $R^5$ is a group represented by the formula (2), $R^2$ and $R^5$ are both not hydrogen atoms;

$R^4$ represents a group represented by the formula (2), and X represents an alkylene group having 4 to 12 carbon atoms or a cycloalkylene group.

2. The 5-fluorouracil compound according to claim 1, wherein said alkanoyl group having 1 to 13 carbon atoms, aralkylcarbonyl group or aroyl group is a group selected from the group consisting of formyl, acetyl, propionyl, butyryl, isobutyryl, pentanoyl, hexanoyl, octanoyl, 2-propylpentanoyl, decanoyl, undecanoyl, dodecanoyl, tridecanoyl, phenylacetyl, 2-chlorophenylacetyl, 3-chlorophenylacetyl, 4-chlorophenylacetyl, 2-bromophenylacetyl, 3-bromophenylacetyl, 4-bromophenylacetyl, 2-fluorophenylacetyl, 3-fluorophenylacetyl, 4-fluorophenylacetyl, 2methylphenylacetyl, 3-methylphenylacetyl, 4-methylphenylacetyl, 2-methoxyphenylacetyl, 3-methoxyphenylacetyl, 4-methoxyphenylacetyl, 2-nitrophenylacetyl, 3-nitrophenylacetyl, 4-nitrophenylacetyl, 1-naphthylacetyl, 2-naphthylacetyl, 2-phenylpropionyl, 3-phenylpropionyl, 2-phenylbutyryl, 3-phenylbutyryl, 4-phenylbutyryl, benzoyl, 2-chlorobenzoyl, 3-chlorobenzoyl, 4-chlorobenzoyl, 2,4-dichlorobenzoyl, 2,5-dichlorobenzoyl, 2,6-dichlorobenzoyl, 3,4,5-trichlorobenzoyl, 2-bromobenzoyl, 3-bromobenzoyl, 4-bromobenzoyl, 2-fluorobenzoyl, 3-fluorobenzoyl, 4-fluorobenzoyl, 2-methylbenzoyl, 3-methylbenzoyl, 4-methylbenzoyl, 2,4-dimethylbenzoyl, 2,5-dimethylbenzoyl, 3,4-dimethylbenzoyl, 3,5-dimethylbenzoyl, 2,6-dimethylbenzoyl, 2-methoxybenzoyl, 4-methoxybenzoyl, 2,4-dimethoxybenzoyl, 2,5-dimethoxybenzoyl, 2,6-dimethoxybenzoyl, 3,4-dimethoxybenzoyl, 3,5-dimethoxybenzoyl, 3-cyanobenzoyl, 4-cyanobenzoyl, 2-acetylbenzoyl, 4-acetylbenzoyl, 2-nitrobenzoyl, 3-nitrobenzoyl, 4-nitrobenzoyl, 1-naphthoyl and 2-naphthoyl groups.

3. The 5-fluorouracil compound according to claim 1, wherein said $R^6$ is an alkanoyl group having 6 to 13 carbon atoms.

4. The 5-fluorouracil compound according to claim 3, wherein said alkanoyl group is 2-propylpentanoyl group.

5. The 5-fluorouracil compound according to claim 1, wherein said $R^7$ is a straight or branched alkyl group having 1 to 13 carbon atoms selected from the group consisting of methyl, ethyl, propyl, isopropyl, butyl, isobutyl, pentyl, hexyl, octyl, tridecyl and 11-methyldodecyl groups.

6. The 5-fluorouracil derivative according to claim 1, wherein said $R^7$ is a hydrogen atom.

7. The 5-fluorouracil compound according to claim 1, wherein said $R^7$ is a lower alkenyl group selected from the group consisting of vinyl, 1-fluorovinyl, 2-fluorovinyl, 2,2-difluorovinyl, 2-bromovinyl, 2-iodovinyl and allyl groups.

8. The 5-fluorouracil compound according to claim 1, wherein said $R^7$ is said phenyl group to which a lower alkyl, a lower alkenyl or a halogen may be substituted is selected from the group consisting of phenyl, 2-bromophenyl, 3-bromophenyl, 4-bromophenyl, 2-chlorophenyl, 3-chlorophenyl, 4-chlorophenyl, 2-fluorophenyl, 3-fluorophenyl, 4-fluorophenyl, 2-tolyl, 3-tolyl, 4-tolyl, 2,5-dimethylphenyl, 3,5-dimethylphenyl, 4-ethylphenyl and 4-vinylphenyl groups.

9. The 5-fluorouracil compound according to claim 1, wherein said n is 0.

10. The 5-fluorouracil compound according to claim 1, wherein said X is said alkylene group or said cycloalkylene group and is a group selected from the group consisting of tetramethylene, pentamethylene, hexamethylene, heptamethylene, octamethylene, nonamethylene, decamethylene, undecamethylene, 1,2-cyclohexylene, 1,3-cyclohexylene and 1,4-cyclohexylene groups.

11. The 5-fluorouracil compound according to claim 1, wherein said compound is represented by the formula:

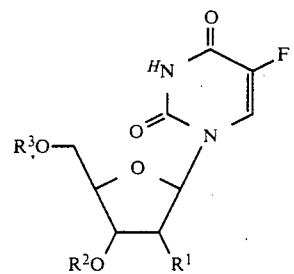

wherein $R^1$, $R^2$ and $R^3$ have the same meanings as defined in claim 1.

12. The 5-fluorouracil compound according to claim 11, wherein said compound is selected from the group consisting of 2′,3′,5′-tris-O-[N-(2-n-propyl-n-pentanoyl)glycyl]-5-fluorouridine, 2′,3′,5′-tris-O-(benzoyl-DL-alanyl)-5-fluorouridine, 2′-deoxy-3′,5′-bis-O-[N-(2-n-propyl-n-pentanoyl)glycyl]-5-fluorouridine, 3′,5′-bis-O-[N-(2-propyl-n-pentanoyl)glycyl] -5-fluorouridine, 2′,3′-bis-O-[N(2-n-propyl-n-pentanoyl)glycyl]-5-fluorouridine and 2′-deoxy-3′-O-[N-(2-n-propyl-n-pentanoyl)glycyl]-5-fluorouridine.

13. The 5-fluorouracil compound according to claim 1 wherein said compound is represented by the formula:

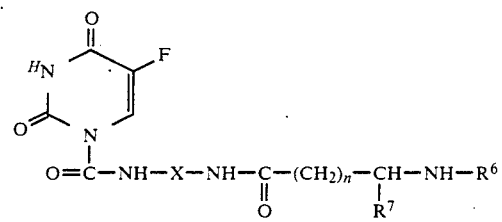

wherein x, $R^6$ and $R^7$ have the same meanings as defined in claim 1.

14. The 5-fluorouracil compound according to claim 13, wherein said compound is selected from the group consisting of 1-[6-[N-(2-propyl-n-pentanoyl)glycyl]amino-n-hexylcarbamoyl]-5-fluorouracil, 1-[5-[N-(2-n-propyl-n-pentanoyl)glycyl]amino-n-pentylcarbamoyl]-5-fluorouracil, 1-[4-[N-(2-n-propyl-n-pentanoyl)glycyl]aminocyclohexylcarbamoyl]-5-fluorouracil and 1-[12-[N-(2-n-propyl-n-pentanoyl)-glycyl]amino-n-dodecylcarbamoyl]-5-fluorouracil.

15. An antitumor agent which comprises the 5-fluorouracil compound represented by the formula (I) as defined in claim 1 as an active ingredient and a pharmacologically acceptable carrier.

* * * * *